United States Patent
Boon et al.

(10) Patent No.: US 8,938,307 B2
(45) Date of Patent: *Jan. 20, 2015

(54) METHOD AND APPARATUS FOR INTRA-BODY ULTRASOUND COMMUNICATION

(71) Applicant: Cardiac Pacemakers, Inc., St. Paul, MN (US)

(72) Inventors: Scot C. Boon, Lino Lakes, MN (US); Keith R. Maile, New Brighton, MN (US); William J. Linder, Golden Valley, MN (US); Paul Huelskamp, St. Paul, MN (US); Ramprasad Vijayagopal, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 36 days.

This patent is subject to a terminal disclaimer.

(21) Appl. No.: 13/648,831

(22) Filed: Oct. 10, 2012

(65) Prior Publication Data

US 2013/0033966 A1 Feb. 7, 2013

Related U.S. Application Data

(63) Continuation of application No. 12/703,427, filed on Feb. 10, 2010, now Pat. No. 8,290,598.

(60) Provisional application No. 61/151,762, filed on Feb. 11, 2009.

(51) Int. Cl.
*A61N 1/36* (2006.01)
*A61N 1/372* (2006.01)
(Continued)

(52) U.S. Cl.
CPC ............ *A61N 1/37217* (2013.01); *H04B 11/00* (2013.01); *H04B 13/005* (2013.01); *A61N 1/3727* (2013.01)
USPC ......................................................... 607/61

(58) Field of Classification Search
None
See application file for complete search history.

(56) References Cited

U.S. PATENT DOCUMENTS

| 5,029,147 A | 7/1991 | Andrews et al. |
| 5,113,859 A | 5/1992 | Funke |

(Continued)

FOREIGN PATENT DOCUMENTS

| WO | WO-0199389 A2 | 12/2001 |
| WO | WO-2010093676 A1 | 8/2010 |

OTHER PUBLICATIONS

"U.S. Appl. No. 12/703,427, Notice of Allowance mailed Jun. 13, 2012", 7 pgs.

(Continued)

*Primary Examiner* — Brian T Gedeon
(74) *Attorney, Agent, or Firm* — Schwegman Lundberg & Woessner, P.A.

(57) ABSTRACT

An intra-body ultrasonic signal can be converted into a first electrical signal, a local oscillator signal can be generated in an implantable system. The first electrical signal and the local oscillator signal can be mixed in an implantable system, such as to generate a demodulated signal, processed, such as using a filter. The filtered, demodulated signal can be further processed, such as implantably determining a peak amplitude of the first portion of the demodulated signal received from the filter over a time interval, implantably generating a dynamic tracking threshold that starts at an amplitude proportional the first portion of the demodulated signal and exponentially decays over a time interval, and determining a noise floor in the absence of a received intra-body ultrasonic signal and implantably comparing the peak amplitude and the tracking threshold and generate the digital output based on the difference.

17 Claims, 7 Drawing Sheets

(51) Int. Cl.
*H04B 11/00* (2006.01)
*H04B 13/00* (2006.01)

(56) References Cited

U.S. PATENT DOCUMENTS

| | | | |
|---|---|---|---|
| 5,139,020 A * | 8/1992 | Koestner et al. | 607/24 |
| 5,263,194 A | 11/1993 | Ragan | |
| 5,383,915 A | 1/1995 | Adams | |
| 5,508,836 A | 4/1996 | DeCaro et al. | |
| 5,620,475 A | 4/1997 | Magnusson | |
| 5,861,018 A | 1/1999 | Feierbach | |
| 6,236,889 B1 | 5/2001 | Soykan et al. | |
| 6,700,514 B2 | 3/2004 | Soltanian et al. | |
| 6,915,083 B1 | 7/2005 | Hamilton et al. | |
| 7,127,224 B2 | 10/2006 | Ichihara | |
| 7,566,308 B2 | 7/2009 | Stahmann | |
| 7,617,001 B2 | 11/2009 | Penner et al. | |
| 7,945,064 B2 | 5/2011 | O'Brien, Jr. et al. | |
| 8,290,598 B2 | 10/2012 | Boon et al. | |
| 2004/0202339 A1 | 10/2004 | O'Brien et al. | |
| 2006/0009818 A1 | 1/2006 | Von Arx et al. | |
| 2006/0064133 A1 | 3/2006 | Von Arx et al. | |
| 2006/0064134 A1 | 3/2006 | Mazar et al. | |
| 2006/0064142 A1 | 3/2006 | Chavan et al. | |
| 2006/0064143 A1 | 3/2006 | Von Arx et al. | |
| 2007/0088221 A1 | 4/2007 | Stahmann | |
| 2008/0165622 A1 | 7/2008 | Liao et al. | |
| 2010/0204758 A1 | 8/2010 | Boon et al. | |

OTHER PUBLICATIONS

"International Application Serial No. PCT/US2010/023729, International Preliminary Report on Patentability mailed Aug. 16, 2011", 5 pgs.

"International Application Serial No. PCT/US2010/023729, International Search Report mailed May 7, 2010", 3 pgs.

"International Application Serial No. PCT/US2010/023729, Written Opinion mailed May 7, 2010", 5 pgs.

Abidi, A. A, "Direct-conversion radio transceivers for digital communications", IEEE Journal of Solid-State Circuits, 30(12), (Sep. 1995), 1399-1410.

Chang, P. J, et al., "A CMOS channel-select filter for a direct-conversion wireless receiver", IEEE Journal of Solid-State Circuits, 32(5), (1997), 722-729.

* cited by examiner

METHOD AND APPARATUS FOR INTRA-BODY ULTRASOUND COMMUNICATION

CLAIM OF PRIORITY

This application is a continuation of and claims the benefit of priority under 35 U.S.C. §120 to Scot Boon et al., U.S. patent application Ser. No. 12/703,427, entitled "Method and Apparatus for Intra-Body Ultrasound Communication," filed on Feb. 10, 2010, now issued as U.S. Pat. No. 8,290,598, which claims the benefit of priority, under 35 U.S.C, §119(e), to Scot Boon et al., U.S. Provisional Patent Application Ser. No. 61/151,762, entitled "Method and Apparatus for Intra-Body Ultrasound Communication," filed on Feb. 11, 2009, the benefit of priority of each of which is claimed hereby, and each of which is hereby incorporated by reference herein in its entirety.

BACKGROUND

Physiological conditions of a subject can provide useful information about the subject's health status, such as to a physician or other caregiver. Sensors or transducers may be implanted for monitoring a variety of properties, such as temperature, pressure, strain, fluid flow, chemical properties, electrical properties, etc. Implantable medical devices (IMDs) may be implanted within a patient's body to monitor, control and communicate physiological conditions received from these sensors or transducers. Some examples of IMDs include, among other things, cardiac function management (CFM) devices such as implantable pacemakers, implantable cardioverter defibrillators (ICDs), cardiac resynchronization devices, and devices that include a combination of such capabilities. Wireless or wired telemetry can be used by IMDs to communicate with implantable sensors or transducers.

OVERVIEW

The present inventors have recognized, among other things, that an implantable device can have limited battery power available. The limited battery power can inhibit the implantable device from easily transmitting, receiving or processing ultrasonic signals, such as used for intra-body communication between the implantable device and one or more other devices. There is a need to place remote sensors in the human body, such as to expand or improve diagnostic capabilities of implantable medical devices (IMD). Wireless communication between the remote sensor and the IMD is highly desirable because wires can, among other things, complicate the implant procedure. In an example, a wireless system provided herein can communicate through, among other things, body tissue, such as using ultrasonic transducers and acoustic pulses. In an example, the power of ultrasonic signal received by the transducers in the remote sensor or the IMD can be very small. Thus, in an example, the receiver used to process the ultrasonic signals can have high gain and low noise levels, such as to enhance reception of low power ultrasonic signals.

Example 1 describes a system. In this example, the system includes an implantable system. In this example, the system includes a first ultrasonic transducer configured to receive an intra-body ultrasonic amplitude-modulated (AM) signal provided by a second implantable ultrasonic transducer and convert the ultrasonic AM signal to a first electrical signal having a first frequency; and an ultrasonic receiver, coupled to the first ultrasonic transducer, configured to receive the first electrical signal and generate a digital output associated with the ultrasonic signal, the ultrasonic receiver including: a local oscillator configured to generate a second electrical signal having a second frequency, a mixer coupled to the local oscillator, configured to mix the received electrical signal and the second electrical signal and generate a demodulated signal, a filter coupled to the mixer, configured to pass a first portion of the demodulated signal having a frequency range with a center frequency equal to the difference between the first frequency and the second frequency; and a detector coupled to the filter and configured to receive the first portion of the demodulated signal, the detector including: a peak detector configured to determine a peak amplitude of the first portion of the demodulated signal received from the filter over a time interval and to determine a noise floor and use the noise floor to dynamically adjust the maximum sensitivity of the detector, a threshold generator to generate a dynamic signal tracking threshold that starts at a value that is proportional to the first portion of the demodulated signal that then exponentially decays over a time interval, and a comparator to compare the peak amplitude and the dynamic signal tracking threshold and generate the digital output based on the difference.

In Example 2, the system of Example 1 optionally includes a preamplifier coupled between the first ultrasonic transducer and the mixer, the preamplifier configured to amplify the first electrical signal received from the first ultrasonic transducer and provide an amplified first electrical signal to the mixer.

In Example 3, the system of Example 2 wherein the preamplifier includes a voltage amplifier.

In Example 4, the system of any one or more of Examples 1-3 is optionally configured such that the second frequency is substantially equal to the first frequency.

In Example 5, the system of any one or more of Examples 1-4 is optionally configured such that the second electrical signal has a frequency in the range of about 1 kHz to about 1 MHz.

In Example 6, the system of any one or more of Examples 1-5 is optionally configured such that the filter includes a switched capacitor filter configured to cancel DC offsets.

In Example 7, the system of Example 6 is optionally configures such that the switched capacitor filter is sampled at a rate that places the maximum attenuation in the frequency response at an unwanted summation product of an output signal received from the mixer.

In Example 8, the system of any one or more of Examples 1-7 is optionally configured such that the preamplifier includes at least one transistor configured to operate in a weak inversion mode.

In Example 9, the system of any one or more of Examples 1-8 is optionally configured such that the first electrical signal received from the transducer is divided into an in-phase (I) channel and a quadrature (Q) channel, to perform quadrature demodulation.

In Example 10, the system of Example 9 is optionally configured such that the in-phase (I) channel includes the mixer and the filter, and the quadrature (Q) channel includes a second mixer and a second filter.

In Example 11, the system of any one or more of Examples 1-10 optionally includes a rectifier to rectify the first portion of the demodulated signal.

In Example 12, the system of any one or more of Examples 1-11 is optionally configured such that an on-off keying (OOK) protocol is used to transmit data having logical ones and zeros.

In Example 13, the system of any one or more of Examples 1-11 is optionally configured such that a frequency shift keying (FSK) modulation scheme is used to transmit data having logical ones and zeros.

In Example 14, the system of any one or more of Examples 1-11, wherein the digital output is optionally used to control an up/down counter, wherein the up/down counter counts up when the output is high and counts down when the output is low, and wherein a specified counter output is used as a threshold value to determine whether a desired signal has been detected.

In Example 15, the system of Examples 14, wherein, upon detecting the desired signal, a time interval is optionally started to prevent further detections.

In Example 16, the system of any one or more of Examples 1-15 is optionally configured such that the second ultrasonic transducer is included in the implantable system.

In Example 17, the system of any one or more of Examples 1-16 optionally includes a pulmonary artery pressure (PAP) sensor that includes the second ultrasonic transducer.

In Example 18, the system of any one or more of Examples 1-16 optionally includes a nerve stimulator that includes the second ultrasonic transducer.

In Example 19, the system of any one or more of Examples 1-16 optionally includes a drug pump that includes the second ultrasonic transducer.

In Example 20, the system of any one or more of Examples 1-19 is optionally configured such that ultrasonic receiver is configured to communicate wirelessly with an external device.

Example 21 describes a method comprising: implantably converting an intra-body ultrasonic signal to a first electrical signal having a first frequency; implantably generating a local oscillator signal, at a second frequency; implantably mixing the first electrical signal and the local oscillator signal to generate a demodulated signal; implantably filtering the demodulated signal to pass a first portion of the demodulated signal having a frequency range with a center frequency equal to the difference between the first frequency and the second frequency; implantably determining a maximum peak amplitude of the first portion of the demodulated signal; implantably generating a dynamic tracking threshold that includes a first portion having an amplitude proportional to the amplitude of the demodulated signal and a second portion where the amplitude exponentially decays over a time interval; implantably determining and establishing a programmable noise floor in the absence of a received intra-body ultrasonic signal; implantably comparing the maximum peak amplitude and the dynamic tracking threshold and generating a digital output based on the difference between the maximum peak amplitude and the dynamic tracking threshold; and implantably limiting the maximum peak amplitude to prevent a sudden large peak which inhibits detection of subsequent peaks.

In Example 22, the method of Example 21 optionally includes amplifying the electrical signal to generate an amplified electrical signal before mixing the carrier signal with the amplified electrical signal.

In Example 23, any one or more of Examples 20-22 is optionally performed such that implantably generating a carrier signal includes implantably generating a carrier signal having a carrier frequency substantially equal to the frequency of the received intra-body ultrasonic signal.

In Examples 24, any one or more of Examples 20-23 is optionally performed by using the maximum peak to adjust dynamically the gain of a filter used for filtering the demodulated signal.

This overview is intended to provide a summary of the subject matter of the present patent application. It is not intended to provide an exclusive or exhaustive explanation of the invention. The detailed description is included to provide further information about the subject matter of the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

This document describes, among other things, systems to receive and methods of receiving low-level ultrasonic signals, such as transmitted from one implantable medical device to another. Additionally, the systems and methods provided herein can provide a low power consumption receiver configured to reduce or minimize noise, such as including self-noise due to thermal or 1/f noise sources. As implantable medical devices typically include limited battery life and thus limited energy, there is a desire to reduce power consumption in a receiver, such as included as a portion of the implantable medical device, used for receiving intra-body communication using ultrasonic signals.

Figure 1:
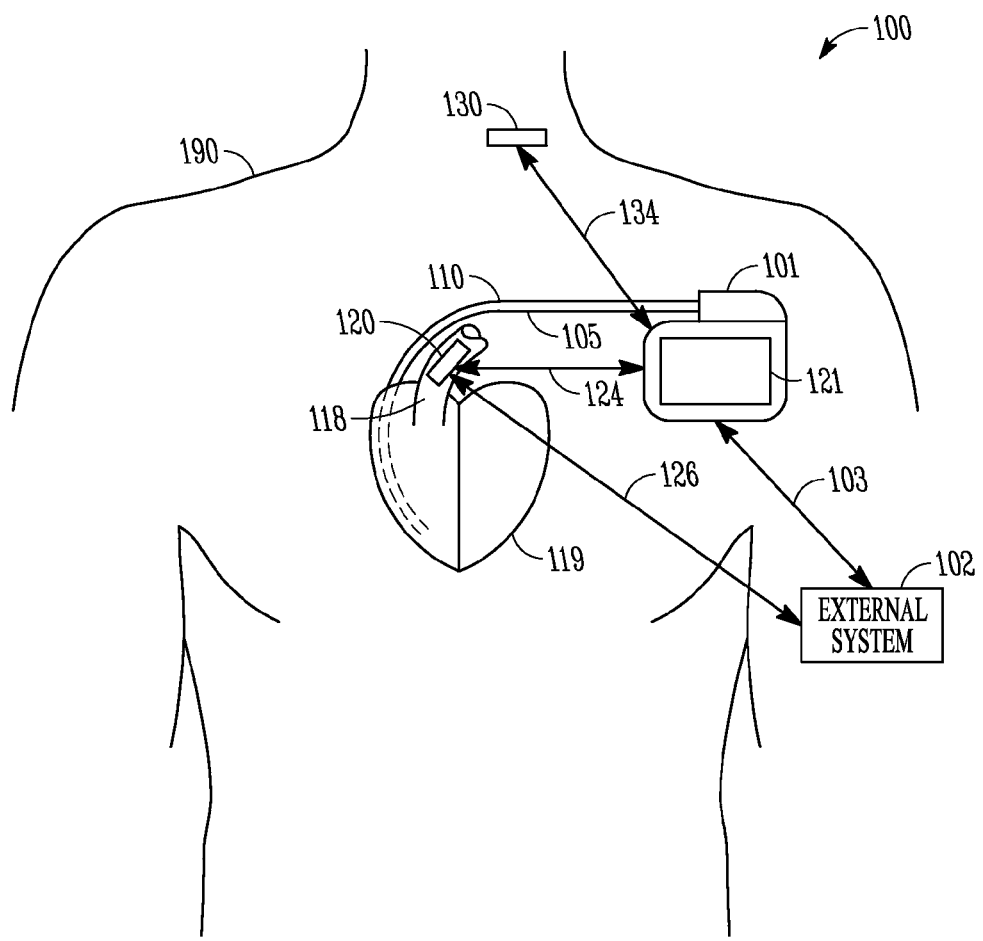
FIG. 1 illustrates an example of a system to process ultrasonic signals used in intra-body ultrasonic communication.

FIG. 1 illustrates an example of an intra-body communication system 100 to process ultrasonic signals and shows portions of an environment in which the system 100 operates. In an example, system 100 includes a first sensor 120, a second sensor 130, an implantable medical device 101, leads 105 and 110, an external system 102, a telemetry link 124 between the sensor 120 and the implantable medical device 101, a telemetry link 134 between the sensor 130 and the implantable medical device 101, a telemetry link 126 between the sensor 120 and the external system 102, and a telemetry link 103 between the implantable medical device 101 and the external system 102.

In an example, the telemetry links 124, 134 include an intra-body wireless telemetry link using ultrasonic signals. An example of an intra-body ultrasonic telemetry system is discussed in U.S. Patent Application Publication No. 2006/0009818, entitled "METHOD AND APPARATUS OF ACOUSTIC COMMUNICATION FOR IMPLANTABLE MEDICAL DEVICE," filed on Jul. 9, 2004, assigned to Cardiac Pacemakers, Inc., which is incorporated herein by reference in its entirety, specifically including its discussion of modulation of acoustic energy for wireless acoustic transfer of information through a body, such as using one or more acoustic transducers coupled to a housing of an implantable medical device.

In an example, the implantable sensor 120 includes a pulmonary arterial pressure (PAP) sensor that is implanted in a pulmonary artery 118 connected to a heart 119. The right ventricle of the heart 119 pumps blood through the pulmonary artery 118 to the lungs of body 190 to oxygenate the blood. The implantable PAP sensor 120 is a pressure sensor configured to be affixed to a portion of the interior wall of the pulmonary artery 118 to sense a PAP signal. The sensed PAP signal is transmitted to the implantable medical device 101 through the telemetry link 124. In an example, the sensed PAP signal is transmitted to the external system 102. Examples of an implantable PAP sensor are described in U.S. patent application Ser. No. 11/249,624, entitled "METHOD AND APPARATUS FOR PULMONARY ARTERY PRESSURE SIGNAL ISOLATION," filed on Oct. 13, 2005, now issued as U.S. Pat. No. 7,566,308, assigned to Cardiac Pacemakers, Inc., which is incorporated herein by reference in its entirety.

The implantable medical device 101 can include an ultrasonic receiver 121 that can receive and process the signal sensed by sensors 120, 130. In an example, the implantable medical device 101 includes a cardiac rhythm management system that is configured to provide one or more of a pacing therapy, a defibrillation therapy, an anti-tachyarrhythmia pacing therapy, a resynchronization therapy, or a neural stimulation therapy. In an example, the implantable medical device 101 further includes one or more of other monitoring and/or therapeutic devices such as a drug or biological material delivery device. The implantable medical device 101 can include a hermetically sealed can housing an electronic circuit, such as to help sense one or more physiological signals or to help deliver one or more therapeutic electrical pulses or other therapies. The hermetically sealed can, in certain examples, can also provide an electrode, such as for electrical sensing or electrical energy delivery.

In some examples, ultrasonic receiver 121 can be implemented by a combination of hardware and software. In some examples, the ultrasonic receiver 121 can include elements such as those referred to as modules below, which can include an application-specific circuit constructed to perform one or more particular functions or a general-purpose circuit that can be programmed to perform one or more functions. Such a general-purpose circuit can include, but is not limited to, a microprocessor or a portion thereof, a microcontroller or portions thereof, or a programmable logic circuit or a portion thereof.

In an example, the telemetry link 124 transmits data representative of the physiological signal sensed by implantable sensor 120 such as to be processed or stored in implantable medical device 101.

The external system 102 can allow programming of the implantable medical device 101 and can receive information about one or more physiologic or other signals acquired by the implantable medical device 101. In an example, the external system 102 can include a programmer. In another example, the external system 102 can include a patient management system, such as an external device (e.g., a repeater) near the implantable medical device 101, a remote device in a relatively distant location from the external device and the implantable medical device 101, and a telecommunication network linking the external device and the remote device.

The patient management system can provide access to the implantable medical device 101 from a remote location, such as for monitoring patient status or adjusting one or more therapies. The telemetry link 103 can include a wireless communication link providing bidirectional data transmission between the implantable medical device 101 and the external system 102. In an example, the telemetry link 103 can include an inductive telemetry link. In another example, telemetry link 103 can include a radio-frequency telemetry link. The telemetry link 103 can provide data transmission from the implantable medical device 101 to the external system 102. This can include, for example, transmitting real-time physiological data acquired by the implantable medical device 101, extracting physiological data acquired by and stored in the implantable medical device 101, extracting therapy history data stored in the implantable medical device 101, or extracting data indicating an operational status of the implantable medical device 101 (e.g., battery status or lead impedance). The telemetry link 103 can also provide data transmission from the external system 102 to the implantable medical device 101. This can include, for example, programming the implantable medical device 101 to acquire physiological data, programming the implantable medical device 101 to perform at least one self-diagnostic test (such as for a device operational status), programming the implantable medical device 101 to enable an available monitoring or therapeutic function, or programming the implantable medical device 101 to adjust one or more therapeutic parameters such as pacing or cardioversion/defibrillation parameters.

Certain examples of sensors, sensor configurations, and communication systems and methods are discussed in more detail in the Mazar et al. U.S. patent application Ser. No. 10/943,626 entitled "SYSTEMS AND METHODS FOR DERIVING RELATIVE PHYSIOLOGIC PARAMETERS," published as US 2006/0064134; the Von Arx et al. U.S. patent application Ser. No. 10/943,269 entitled "SYSTEMS AND METHODS FOR DERIVING RELATIVE PHYSIOLOGIC MEASUREMENTS USING AN EXTERNAL COMPUTING DEVICE," published as US 2006/0064133; the Von Arx et al. U.S. patent application Ser. No. 10/943,627 entitled "SYSTEMS AND METHODS FOR DERIVING RELATIVE PHYSIOLOGIC PARAMETERS USING A BACK-END COMPUTING SYSTEM," now issued as U.S. Pat. No. 8,271,093; and the Chavan et al. U.S. patent application Ser. No. 10/943,271 entitled "SYSTEMS AND METHODS FOR DERIVING RELATIVE PHYSIOLOGIC PARAMETERS USING AN IMPLANTED SENSOR DEVICE," published as US 2006/0064142; and the U.S. patent application Ser. No. 10/943,271 entitled "SYSTEMS AND METHODS FOR DERIVING RELATIVE PHYSIOLOGIC MEASUREMENTS USING AN IMPLANTED SENSOR DEVICE," all assigned to Cardiac Pacemakers, Inc., all of which are incorporated herein by reference in their entirety, and which are collectively referred to as the "Physiologic Parameter Sensing Systems and Methods Patents" in this document.

In an example, the receiver 121 can be configured to detect an ultrasonic signal correlating to at least one PA pressure characteristic, such as a PA diastolic pressure ("PAD"), a PA systolic pressure ("PAS"), a mean (or other central tendency) PAP, a PA end-diastolic pressure ("PAEDP"), a rate of pressure change in the PA ("PA dP/dt"), a PA pulse pressure ("PAPP"), or other PA pressure characteristic, using PAP information, such as the PAP signal, from the sensor 120.

In an example, receiver 121 can be configured to detect at least one ultrasonic signal correlative to at least one LV pressure characteristic, such as a LV pressure, a LV diastolic pressure, a LV systolic pressure, a LVEDP, a mean (or other central tendency) LV pressure, a LV volume, a LV dP/dt, or other LV pressure characteristic, such as by using PAP information from the sensor 120. In an example, sensor 120 is disposed in the aorta to detect at least one LV pressure characteristic.

The following discussion provides examples of physiological sensors that that can be included in the system 100 in conjunction with transducers to generate ultrasonic signals. The generated ultrasonic signals correlate to one or more physiological characteristics sensed by the physiological sensor.

In one example, a heart sound sensor can be configured to sense information indicative of one or more heart sounds within body 190. A "heart sound" can include a first heart sound ("S1"), a second heart sound ("S2"), a third heart sound ("S3"), a fourth heart sound ("S4"), or any components thereof, such as the aortic component of S2 ("A2"), the pulmonary component of S2 ("P2"), or other broadband sounds or vibrations associated with valve closures or fluid movement, such as a heart murmur, etc. Heart sounds can also include one or more broadband chest sounds, such as may result from one or more of mitral regurgitation, left ventricle dilation, etc. The heart sound sensor typically provides an electrical "heart sound signal" that includes heart sound information which is then converted into an ultrasonic signal and transmitted using a transducer. The heart sound sensor can include any device configured to sense the heart sound signal of the subject. In certain examples, the heart sound sensor can include an implantable sensor including at least one of an accelerometer, an acoustic sensor, a microphone, etc. Typically, the frequency range of desired heart sounds include from about 2 Hz to about 1000 Hz.

In another example, a lung sounds sensor can be configured to sense a signal representing the lung sound of subject. Broad-band chest sounds are useful for heart failure patient management. Detection of lung sounds helps the implantable device to provide more appropriate and optimal therapy. The lung sound signal can include any signal indicative of at least a portion of at least one lung sound of the subject. The subject's changed pulmonary (lung) sounds (e.g., increased rales and wheezes) is used as a physiologic parameter that is statistically associated with impending thoracic fluid accumulation and/or lung congestion. In one example, an increase in the frequency or amplitude of rales may correlate to a future thoracic fluid accumulation. Additionally, recording these sounds and uploading the recording over an advanced patient management infrastructure can help a doctor to improve disease management.

In another example, a cardiac wall motion sensor can be configured to sense during each cardiac cycle, a signal representing the inward and outward displacement of the ventricular endocardial wall of body 190.

In another example, a neural activity sensor can be configured to sense a signal representing the nerve activity in or around the pulmonary artery by at least one electrode intravascularly inserted into the pulmonary artery of body 190.

In another example, a blood pressure sensor can be configured to sense a signal representing the pressure inside at least one of the atriums or ventricles of the heart, pulmonary artery or any blood vessel of body 190.

In an example, the ultrasonic telemetry links 124, 134 are configured to use parity bits and cyclic redundancy checks (CRCs) that can detect and correct potential errors that are introduced in the data between the implantable sensor 120 and the implantable medical device 101.

Figure 2:
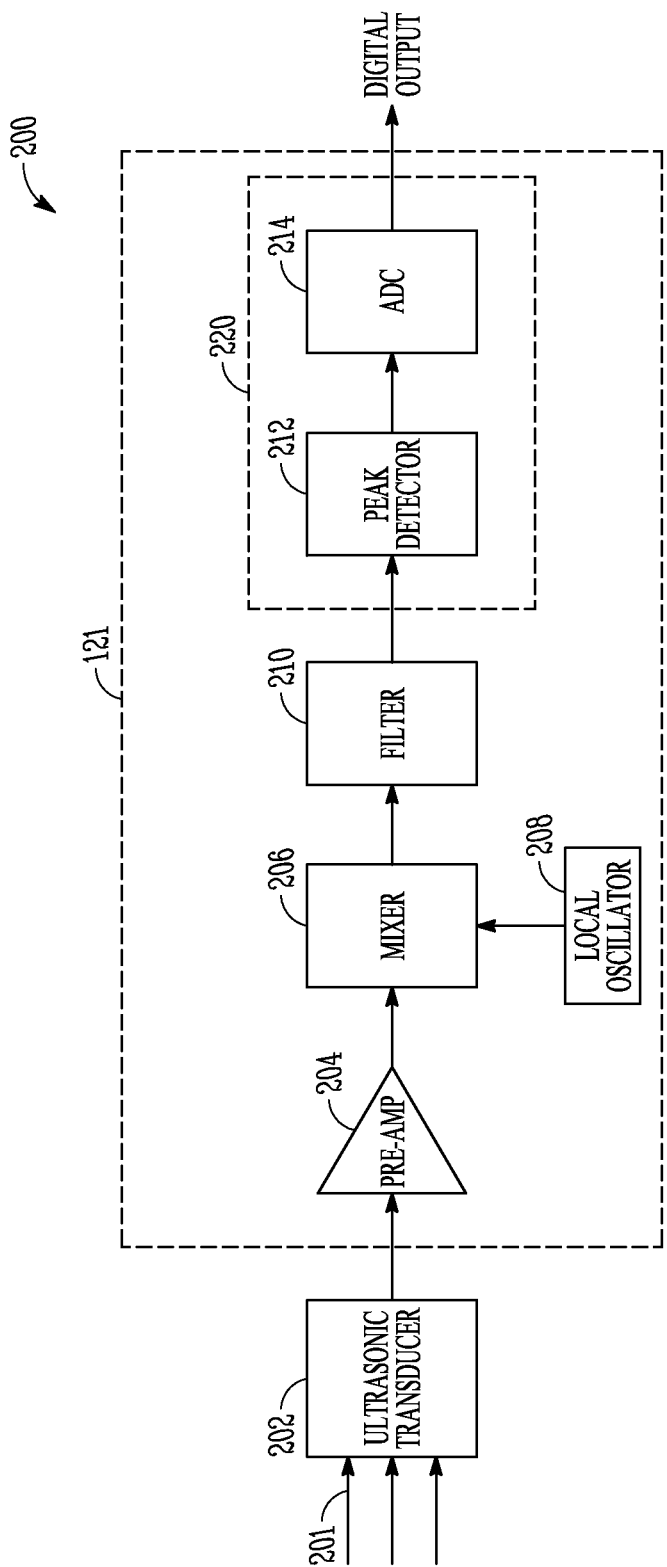
FIG. 2 illustrates an example of system including a receiver used for intra-body ultrasonic communication.

FIG. 2 illustrates an example of a communication system 200 used for intra-body communication. In an example, system 200 includes an ultrasonic transducer 202 and an ultrasonic receiver 121. In an example, ultrasonic transducer 202 can be implantable and configured to receive ultra-sound signals from at least one sensor or a separate implantable medical device (IMD) disposed within the body and generate electrical signal analogous to the received ultra-sound signal.

In an example, ultrasonic receiver 121 includes a preamplifier 204, a mixer 206, a local oscillator 208, a filter 210 and a detector 220. In an example, preamplifier 204 can be electrically coupled to the ultrasonic transducer 202 and mixer 206. In an example, mixer 206 can be coupled to the local oscillator 208 and the filter 210. In an example, filter 210 can be coupled to the detector 220. In an example, detector 220 includes a peak detector 212 and an analog to digital converter (ADC) 214. In an example, the peak detector 212 is coupled to ADC 214, and the ADC 214 provides a digital output, which corresponds to the largest peaks of the ultrasonic signal 201. In an example, the digital out put from ADC 214 is used to perform automatic gain control. In an example, ADC 214 is a one-bit ADC. In an example, the ADC 214 is configured to provide a noise peak measurement for setting a threshold for the noise floor.

In an example, the preamplifier 204 includes a voltage amplifier, which does not require a capacitive feedback circuit that may be typically found in charge amplifiers. As a result, in contrast to a charge amplifier, the voltage amplifier has reduced current consumption from the power source (e.g. battery source within an implantable device) than a typical charge amplifier. Moreover, as the ultrasonic transducer 202 is terminated at the input of the preamplifier 204, the termination resistance serves to dissipate any charge that may be generated by mechanical stress or by other means. In addition, the use of such voltage amplifiers with input termination provide for the formation of a high pass pole in conjunction with the transducer, which allows for diminishing the 1/f noise.

Figure 3A:
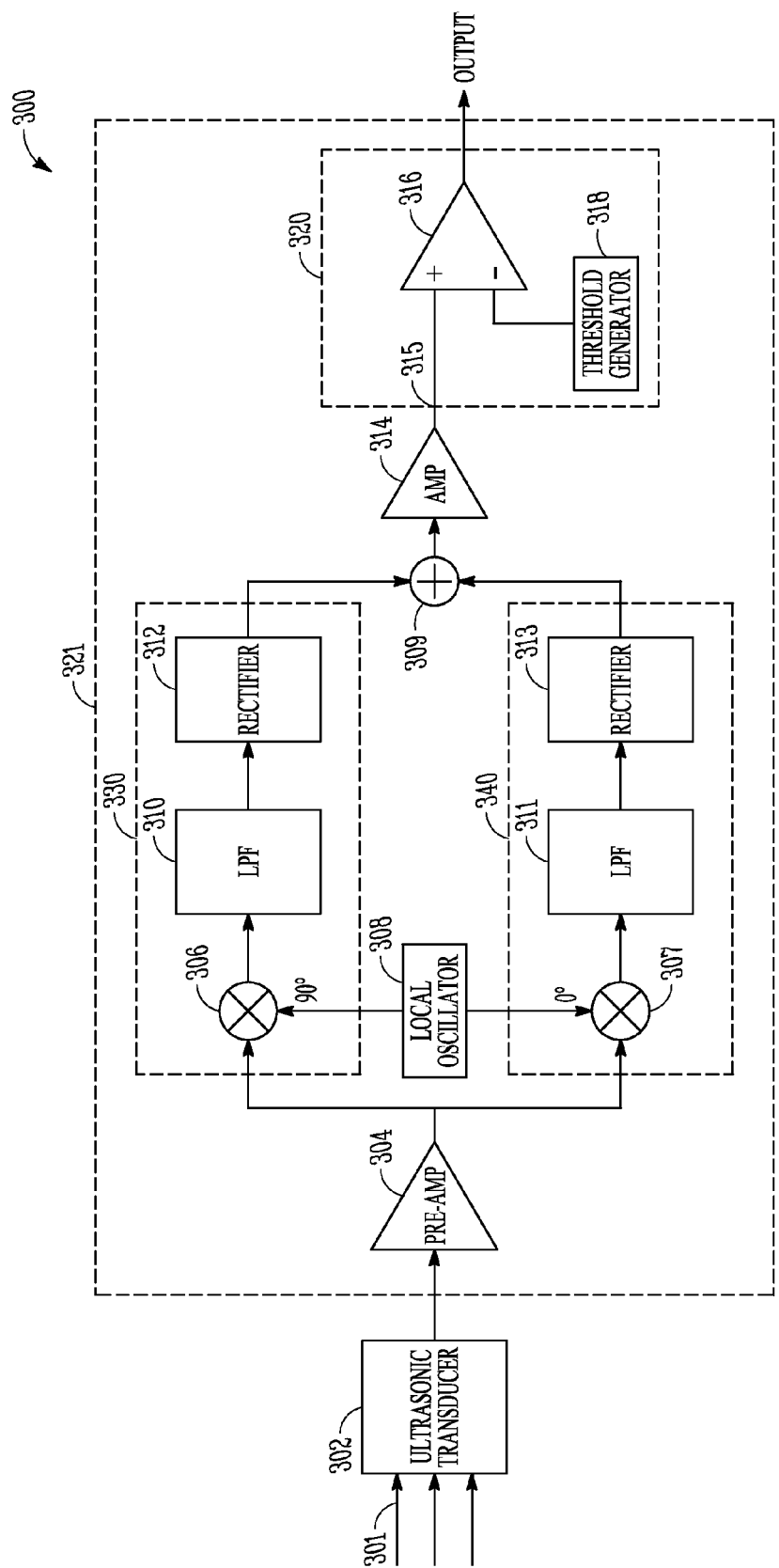
FIG. 3A illustrates an example of a system including a direct conversion receiver that provides intra-body ultrasonic communication.

FIG. 3A illustrates an example of a communication system 300 including a direct conversion ultrasonic receiver used for intra-body communication. In an example, system 300 includes an ultrasonic transducer 302 and an ultrasonic receiver 321. In an example, ultrasonic transducer 302 can be configured to receive an ultra-sound signal from at least one sensor or IMD disposed within the body and generate electrical signal corresponding to the received ultra-sound signal 301.

In an example, receiver 321 includes a preamplifier 304, a first signal channel (I-channel) 330, a second signal channel (Q-channel) 340, a local oscillator 308, a post-amplifier 314 and a detector 320. In an example, the transducer 302 can be coupled to preamplifier 304. In an example, the first channel 330 and the second channel 340 can be coupled between the preamplifier 304 and the post-amplifier 314. In an example, the first channel 330 includes a mixer 306, a filter 310 and a rectifier 312; and the second channel 340 includes a mixer 307, a filter 311 and a rectifier 313. In an example, the rectifier 312 and the rectifier 313 are coupled to a summer 309. In an example, the summer 309 is coupled to post-amplifier 314, which is coupled to detector 320. In an example, detector 320 includes a threshold generator 318 and a comparator 316. In an example, the comparator 316 receives signals from the post-amplifier 314 and the threshold generator 318 and compares the signals to generate an output.

In an example, the local oscillator 308 provides a first local oscillator signal to mixer 306 and a second local oscillator signal to mixer 307. In one example, the first local oscillator signal provided to mixer 306 is 90 degrees out-of-phase with the second local oscillator signal provided to mixer 307. In one example, the first local oscillator signal has the same frequency as the second local oscillator signal. In one example, the frequency of the signal generated at the local oscillator is substantially the same as the frequency of the signal received from the preamplifier 304. In one example, the frequency of the signal generated at the local oscillator is in the range of about 1 kHz to about 1 MHz.

In an example, the preamplifier 304 amplifies the electrical signal generated by the ultrasonic transducer 302, which is related to the ultrasonic signal 301 received at transducer 302.

In one example, the preamplifier 304 includes a field effect transistor (FET) that is operated in a weak inversion mode thereby using approximately 40% of the power that is needed by a transistor operated in a strong inversion mode. In an example, the voltage amplifier includes about four cascaded AC-coupled amplifier stages. Providing AC-coupling prevents the accumulation of offsets that would otherwise saturate the amplifiers.

Any coupling from the local oscillator 308 into the preamplifier 304 can cause offsets (e.g., voltage offsets) at the outputs of mixers 306, 307. In an example, these offsets are cancelled following the mixers 306, 307 by coupling capacitors that are switched to ground between transmissions. In an example, these offsets are stored on the coupling capacitors prior to and potentially periodically during data communication and subtracted during normal receiver operation.

In an example, filters 310 and 311 include a switched capacitor filter configured to cancel DC offsets both prior to and potentially periodically during data communication. In an example, the switched capacitor filter narrows the baseband of the signals received from mixers 306, 307 to reduce the noise. In one example, by setting the sampling clock frequency to about four-times the carrier frequency, the sum mixer product at two-times the carrier frequency is attenuated. A switched capacitor filter will produce replicas of the transfer function at integer multiples of the sampling clock frequency. Therefore, a low-pass transfer function (similar to that shown in FIG. 3B) can have a minima at half the sampling clock frequency, where the attenuated response meets the first replica.

Figure 3B:
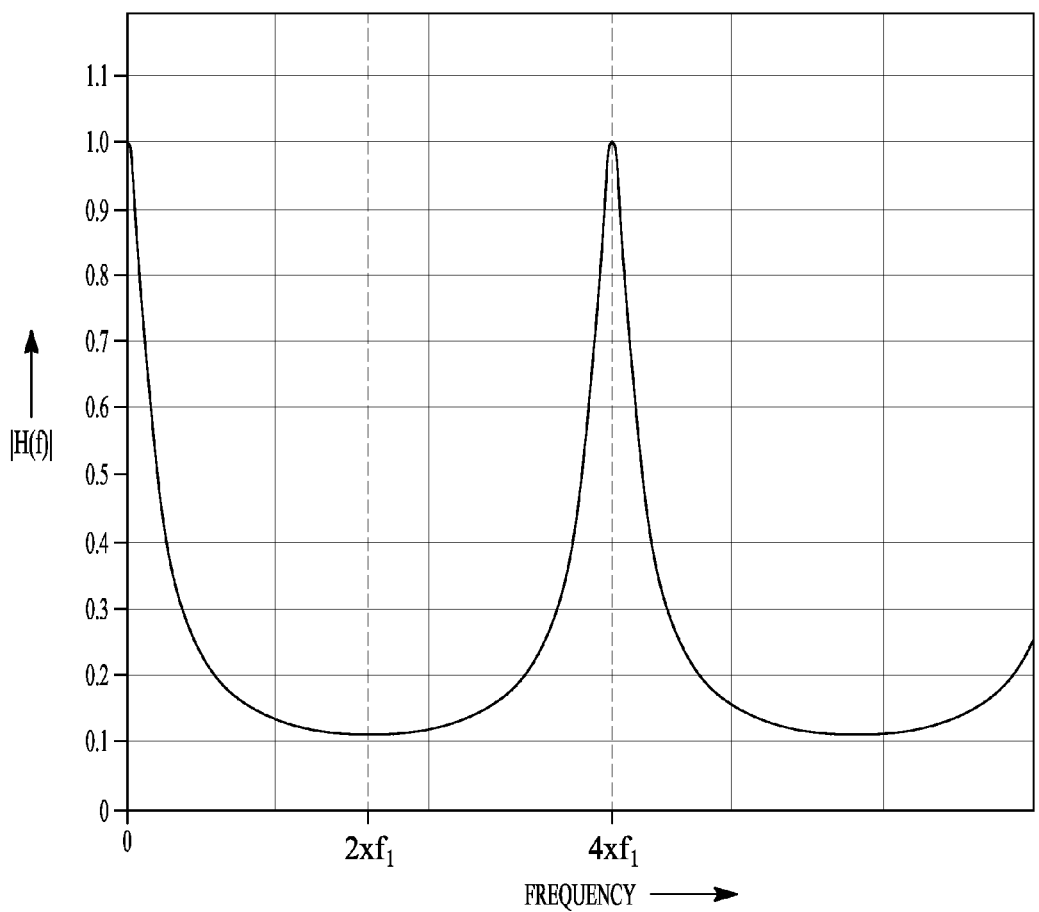
FIG. 3B illustrates an example of a filter transfer function for the filters shown in FIG. 3A.

FIG. 3B illustrates an example of a filter transfer function for any of the filters 310 and 311 provided in FIG. 3A. FIG. 3B shows peaks at 0 Hz and 4 $f_{carrier}$ and a local minimum located at 2 $f_{carrier}$.

In one example, filters 310 and 311 are low pass filters. In one example, filters 310 and 311 are band-pass filters. In one example, filters 310 and 311 are provided with digitally programmable gain control.

In an example, the rectifiers 312 and 313 rectify the output signals from filters 310 and 311, respectively. In one example, rectifiers 312 and 313 perform rectification by using zero-crossing comparators and analog multiplexers. In one example, the use of rectifiers instead of performing root-mean-square (RMS) function allows for a simpler design that saves both power and chip area.

In an example, detector 320 includes a peak detector that is used to acquire the largest signal excursion over a defined interval. When no signal is being received, the peak detector output is digitized by an analog-to-digital (ADC) to determine the maximum noise floor, which is subsequently used to establish the minimum detection threshold. During signal reception, the maximum reading is used in an automatic gain control (AGC) feedback loop to adjust receiver gain. Gain is adjusted in the preamplifier 304, filters (310, 311) and post-amplifier or summing amplifier, 314.

In an example, a programmable number of preamplifier stages can be used that allows for digital automatic gain control (AGC). In an example, the preamplifier stages provided are fully differential to enhance the common mode rejection ratio (CMRR) and the power supply rejection ratio (PSRR) performance. In an example, a down conversion architecture can be implemented using field effect transistor (FET) based double balanced mixers. In this double balanced mixer the differential carrier signal from the preamplifier is steered by the gate drive on the FETs such that it is inverted on one phase of the local oscillator and not inverted on the other phase.

In an example, a digital output of receiver 321 is used to control an up/down counter, such that the counter counts upwards when the output is high and counts downward when the output is low. A specified output of the counter is used as a threshold to determine whether a signal has been detected. The counter is initialized at the start of a detection window. The counter will maintain a buffer of the last N samples. If the sample coming in and leaving are the same, the counter will not change. If the sample coming in is active and the sample leaving is not active, the counter will be advanced but not overflow. If the sample coming in is not active and the sample leaving is active, the counter will be decreased but not underflow.

Figure 4A:
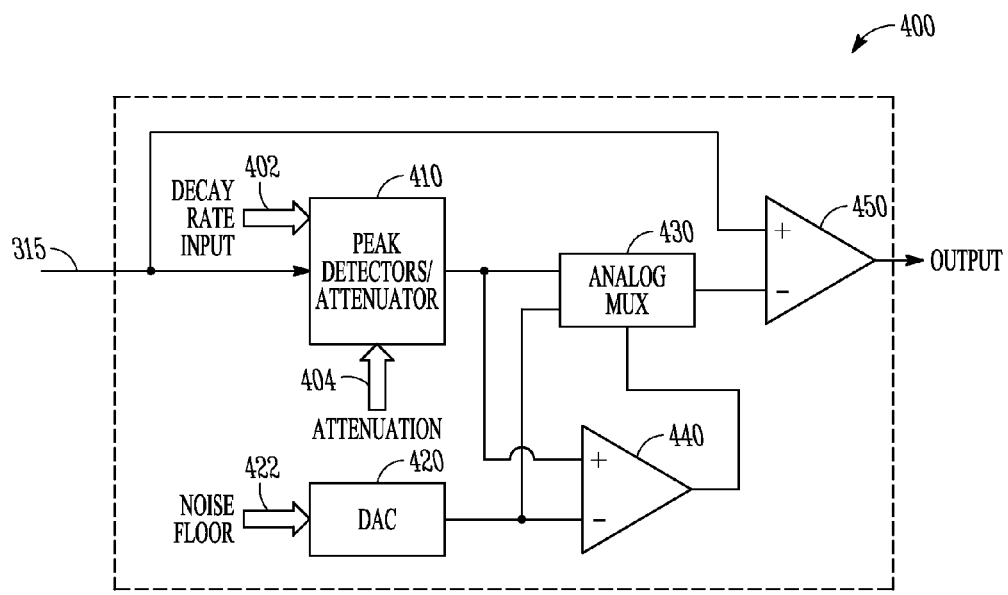
FIG. 4A illustrates an example of a detector used in a receiver that provides intra-body ultrasonic communication.

FIG. 4A illustrates an example of a detector 400 used in an ultrasonic receiver for intra-body ultrasonic communication. In an example, detector 400 includes a peak detector 410, a digital-to-analog converter (DAC) 420, an analog multiplexer 430, and comparators 440 and 450. In an example, ultrasonic receiver 321 receives an input 315 from post-amplifier 314, which provides an analog output that corresponds to the demodulated ultrasonic signal received at transducer (202, 302). In an example, peak detector 410 tracks positive-going signals with little delay while negative-going signals decay exponentially to the common mode level. In an example, the peak detector 410 output is also attenuated to assure a threshold that is lower than the post-amplifier 314 output. In an example, the noise floor is set using DAC 420. In an example, comparator 440 determines whether the signal from the peak detector 410 or the DAC 420 is larger and selects the larger threshold at analog multiplexer 430. In some examples, the effect of a sudden large peak, for example from a cough generated by the patient, is limited by the saturation level of the output of post-amplifier 314. In an example, a threshold signal can be generated that tracks the post-amplifier output 314 on the rising edge and decays at an attenuated level until it reaches the noise floor provided by the DAC 420. This detection method reduces the susceptibility to acoustic reverberations and amplitude variations, which are characteristic of an acoustic communication channel in an implanted environment.

Figure 4B:
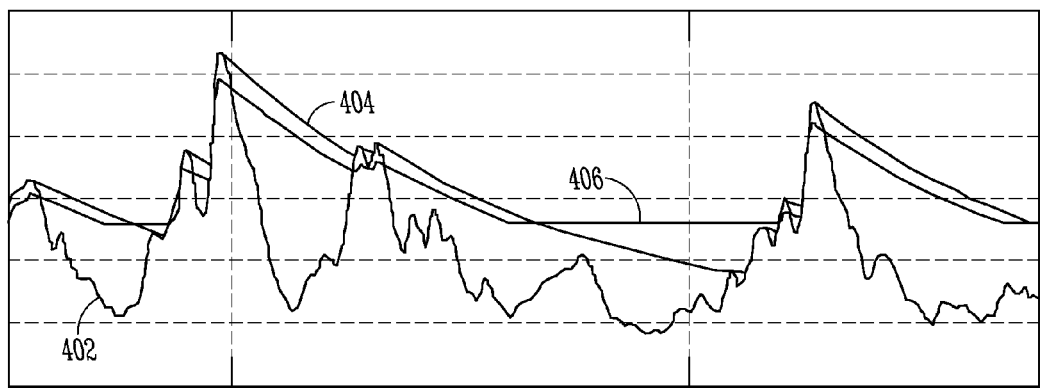
FIG. 4B illustrates an example of the waveforms of signals at the detector shown in FIG. 4A.

FIG. 4B illustrates an example of the waveforms of signals at the detector 400 shown in FIG. 4A. Signal 402 corresponds to the output of post-amplifier 314. Signal 404 corresponds to the output of the peak detector 410 output. Signal 406 is the threshold output of the analog multiplexer 430, which shows that the threshold flatten out when it reaches the noise floor set by the DAC 420.

Figure 5:
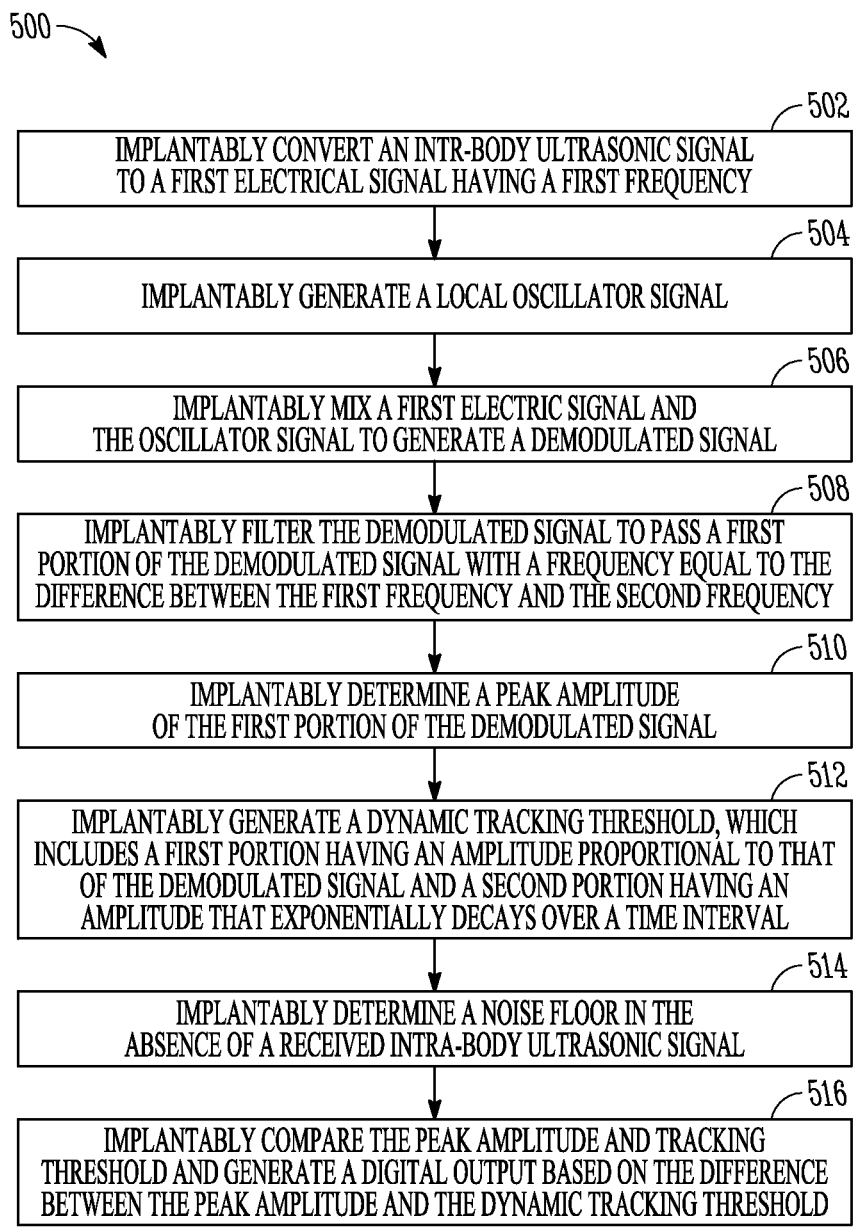
FIG. 5 illustrates an example of a method of providing intra-body ultrasonic communication.

FIG. 5 illustrates an example of a method 500 of providing intra-body ultrasonic communication.

At 502, the method 500 includes implantably converting an intra-body ultrasonic signal to an electrical signal having a first frequency ($f_1$ Hz). In an example, the ultrasonic signal can be communicated to the implantable medical device 101 of FIG. 1 by the sensor 120. In an example, sensor 120 includes a transducer that can generate the ultrasonic signal, which is communicated to the implantable medical device 101.

At 504, the method 500 can include implantably generating a local oscillator signal. In one example, the local oscillator signal is generated by local oscillator 208. In an example, the local oscillator signal has a frequency that is substantially the same as the first frequency ($f_1$ Hz).

At 506, the method 500 can include implantably mixing the first electrical signal and the local oscillator signal to generate a demodulated signal. In one example, the first electrical signal and the local oscillator signal is mixed using a mixer 206 as in FIG. 2.

At 508, the method 500 can include implantably filtering the demodulated signal to pass a first portion of the demodulated signal. The first portion has a frequency range with a center frequency equal to the difference between the first frequency and the second frequency.

At 510, the method 500 can include implantably determining a peak amplitude of the first portion of the demodulated signal. In an example, the peak amplitude is detected using a peak detector 212.

At 512, the method 500 can include implantably generating a dynamic tracking threshold that includes a first portion having an amplitude proportional to the amplitude of the demodulated signal and a second portion where the amplitude exponentially decays over a time interval.

At 514, the method 500 can include implantably determining a noise floor in the absence of a received intra-body ultrasonic signal.

At 516, the method 500 can include implantably comparing the peak amplitude and the dynamic tracking threshold and generate a digital output based on the difference between the peak amplitude and the dynamic tracking threshold.

Figure 6:
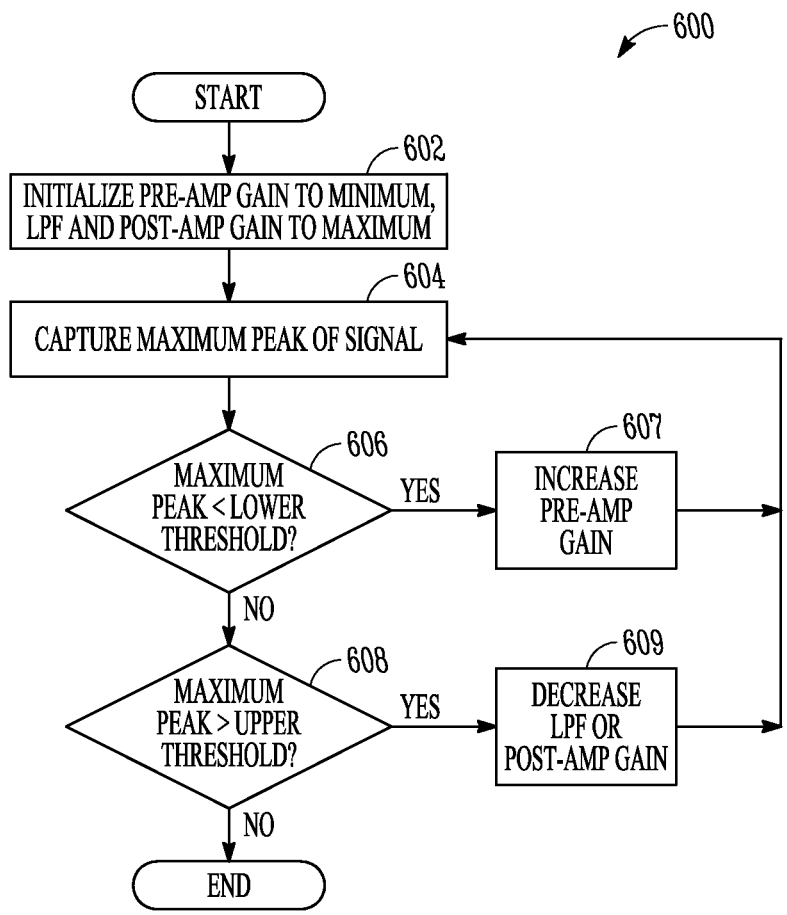
FIG. 6 illustrates an example of a method for providing automatic gain control for a receiver that provides intra-body ultrasonic communication.

FIG. 6 illustrates an example of a method 600 for providing automatic gain control for a receiver that provides intra-body ultrasonic communication.

At 602, the method 600 includes initializing the gain of a preamplifier 304 to a minimum gain value and initializing the gain of filters 310, 311 and the gain of post-amplifier 314 to a maximum gain value.

At 604, the method 600 can include capturing a maximum peak of a signal received by detector 220, 320. In an example, the maximum peak is captured using peak detector 212. In an example, the maximum peak is captured using a comparator 316 coupled to a threshold generator 318 as shown in FIG. 3A.

At 606, the method 600 can include comparing the captured maximum peak to a lower threshold. If the maximum peak is less than the lower threshold, the method 600 proceeds to 607. If the maximum peak is greater than the lower threshold then the method 600 proceeds to 608. In one example, the lower threshold includes an amplitude that is about two-thirds of the maximum peak.

At 607, the method 600 can include increasing the gain of the preamplifier 204, 304.

At 608, the method 600 can include comparing the maximum peak to an upper threshold. If the maximum peak is greater than the upper threshold then the method 600 proceeds to 609. In one example, the upper threshold includes an amplitude about one-third of the maximum peak. If the maximum peak is less than the upper threshold then the method 600 terminates.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be deter-

What is claimed is:

1. An implantable system, comprising:
    an ultrasonic receiver circuit coupleable to an ultrasonic transducer, the ultrasonic receiver circuit configured to obtain from the ultrasonic transducer a first electrical signal representative of an ultrasonic communication signal transduced by the ultrasonic transducer, the ultrasonic receiver circuit comprising:
    a local oscillator circuit;
    a mixer circuit coupled to the local oscillator circuit, the mixer circuit configured to provide a second electrical signal representative of the ultrasonic communication signal using the first electrical signal and the local oscillator circuit;
    a pre-amplifier circuit coupled to the mixer circuit, the pre-amplifier circuit including at least one field-effect transistor (FET) configured to operate in a weak inversion mode; and
    an analog-to-digital converter circuit coupled to the mixer and configured to provide a digital representation of the second electrical signal.

2. The implantable system of claim 1, wherein the pre-amplifier circuit comprises a voltage-mode pre-amplifier circuit coupled to the mixer circuit and coupleable to the ultrasonic transducer, the pre-amplifier circuit configured to at least one of amplify or buffer the first electrical signal, and to provide at least one of a buffered or amplified first electrical signal to the mixer circuit.

3. The implantable system of claim 1, comprising a filter circuit coupled to the mixer circuit and the analog-to-digital converter circuit, the filter circuit configured to inhibit or suppress passage of a portion of second electrical signal from the mixer circuit to the analog-to-digital converter.

4. The implantable system of claim 3, wherein the filter circuit is configured to pass a first portion of the second electrical signal including a frequency range corresponding to respective differences between a first range of frequencies included in the first signal and a local oscillator frequency; and
    wherein the filter circuit is configured to inhibit or suppress passage of a second portion of the second electrical signal corresponding to respective sums of the first range of respective frequencies included in the first signal and local oscillator frequency.

5. The implantable system of claim 3, wherein the filter circuit is configured to inhibit or suppress passage of a DC component of the second electrical signal.

6. The implantable system of claim 3, wherein the filter circuit comprises a switched-capacitor filter circuit.

7. The implantable system of claim 6, wherein the switched capacitor filter circuit is switched at a rate established at least in part to inhibit or suppress a specified range of frequencies in the second electrical signal corresponding to an unwanted summation product of the first range of respective frequencies included in the first signal and the local oscillator frequency.

8. The implantable system of claim 1, wherein the ultrasonic communication signal includes an amplitude-modulated communication signal; and
    wherein the receiver circuit includes a detector circuit coupled to the mixer and configured to demodulate amplitude-modulated information included in the second electrical signal.

9. The implantable system of claim 1, wherein the ultrasonic receiver circuit comprises a threshold comparator coupled to the mixer and configured to compare the second electrical signal with a specified threshold.

10. The implantable system of claim 9, wherein the specified threshold is adjustable and is established at least in part using a threshold generator circuit configured to determine information about a peak level in the second electrical signal and configured to establish the specified threshold using information about the peak level.

11. The implantable system of claim 1, wherein the ultrasonic receiver circuit is configured to generate an in-phase (I) representation of the second electrical signal, and a quadrature (Q) representation of the second electrical signal.

12. The implantable system of claim 1, wherein the ultrasonic communication signal includes a frequency-shift keyed communication signal.

13. The implantable system of claim 1, wherein the ultrasonic communication signal includes information obtained from one or more implantable sensors.

14. The implantable system of claim 1, further comprising the ultrasonic transducer.

15. The implantable system of claim 1, wherein the ultrasonic receiver is configured to receive a communication signal generated from a location within the body.

16. The implantable system of claim 1, wherein the ultrasonic receiver is configured to receive a communication signal generated from a location external to the body.

17. A method, comprising:
    obtaining a first electrical signal from an ultrasonic transducer, the first electrical signal representative of an ultrasonic communication signal transduced by the ultrasonic transducer;
    using a pre-amplifier circuit to provide at least one of a buffered or amplified first electrical signal to a mixer circuit including operating at least one field-effect transistor (FET) in a weak-inversion mode;
    providing a second electrical signal by mixing a local oscillator signal and the buffered or amplified first electrical signal using the mixer circuit; and
    digitizing the second electrical signal.

* * * * *